(12) United States Patent
Robinson

(10) Patent No.: US 6,767,494 B1
(45) Date of Patent: Jul. 27, 2004

(54) METHOD AND APPARATUS FOR INJECTION MOLDING A THREADED SYRINGE PLUNGER ROD

(75) Inventor: Philip J. Robinson, Sylvania, OH (US)

(73) Assignee: Owens-Illinois Closure Inc., Toledo, OH (US)

(*) Notice: Subject to any disclaimer, the term of this patent is extended or adjusted under 35 U.S.C. 154(b) by 130 days.

(21) Appl. No.: 10/236,241

(22) Filed: Sep. 6, 2002

Related U.S. Application Data

(62) Division of application No. 09/826,584, filed on Apr. 5, 2001, now Pat. No. 6,494,866.

(51) Int. Cl.[7] .......................... B29C 45/18; B29C 45/44
(52) U.S. Cl. ................... 264/318; 264/328.9; 425/556; 425/577; 425/DIG. 58; 249/59
(58) Field of Search ............................ 264/328.1, 328.9, 264/328.12, 318; 425/577, DIG. 58, 556; 249/59

(56) References Cited

U.S. PATENT DOCUMENTS

| | | | | |
|---|---|---|---|---|
| 2,306,205 A | * | 12/1942 | Crosman, Jr. | ........ 425/DIG. 58 |
| 3,402,713 A | * | 9/1968 | Senkowski et al. | ......... 264/318 |
| 3,729,032 A | | 4/1973 | Tischlinger et al. | |
| 3,965,898 A | | 6/1976 | Cloyd | |
| 4,048,997 A | | 9/1977 | Raghavachari et al. | |
| 4,370,982 A | | 2/1983 | Reilly | |
| 4,655,749 A | | 4/1987 | Fischione | |
| 4,747,829 A | | 5/1988 | Jacob et al. | |
| 4,886,495 A | | 12/1989 | Reynolds | |
| 5,009,587 A | * | 4/1991 | Corvaglia et al. | ..... 264/328.12 |
| 5,032,114 A | | 7/1991 | Olovson | |
| 5,093,878 A | * | 3/1992 | Haley et al. | ............. 264/328.1 |
| 5,094,148 A | | 3/1992 | Haber et al. | |
| 5,249,711 A | * | 10/1993 | Filbert, Jr. | .................. 604/295 |
| 5,411,488 A | | 5/1995 | Pagay et al. | |
| 5,411,489 A | | 5/1995 | Pagay et al. | |
| 5,413,563 A | | 5/1995 | Basile et al. | |
| 5,460,617 A | | 10/1995 | Minkus et al. | |
| 5,536,253 A | | 7/1996 | Haber et al. | |
| D383,205 S | | 9/1997 | Pagay et al. | |
| 5,688,252 A | | 11/1997 | Matsuda et al. | |
| 5,702,736 A | * | 12/1997 | Henein | ....................... 425/556 |
| 5,752,940 A | | 5/1998 | Grimard | |
| 5,951,527 A | | 9/1999 | Sudo | |
| 6,123,688 A | | 9/2000 | Botich et al. | |
| 6,129,712 A | | 10/2000 | Sudo et al. | |

* cited by examiner

Primary Examiner—Jill L. Heitbrink

(57) ABSTRACT

A plunger rod for a syringe in is of integrally injection molded plastic construction having an elongated body with a coaxial end portion. An external thread extends around the end portion for threaded receipt into a plunger tip that is slidably received in a syringe barrel. A flat extends chordally across the end portion of the rod body interrupting the external thread. The plastic, of which the plunger rod is molded, is gated into the mold for the plunger rod at the flat that extends across the rod end portion, leaving a gate mark or vestige on the flat. Gating of the plastic material into the portion of the mold that forms the threaded end portion of the plunger rod achieves improved flow and improved filling of the external thread, while employing a simple and economical mold construction. The gate vestige does not interfere with threading of the plunger rod end portion into the plunger tip. The end portion of the plunger rod is cored during molding to provide a C-shaped cross section at the rod end portion, which improves dimensional stability during material shrinkage after molding.

7 Claims, 6 Drawing Sheets

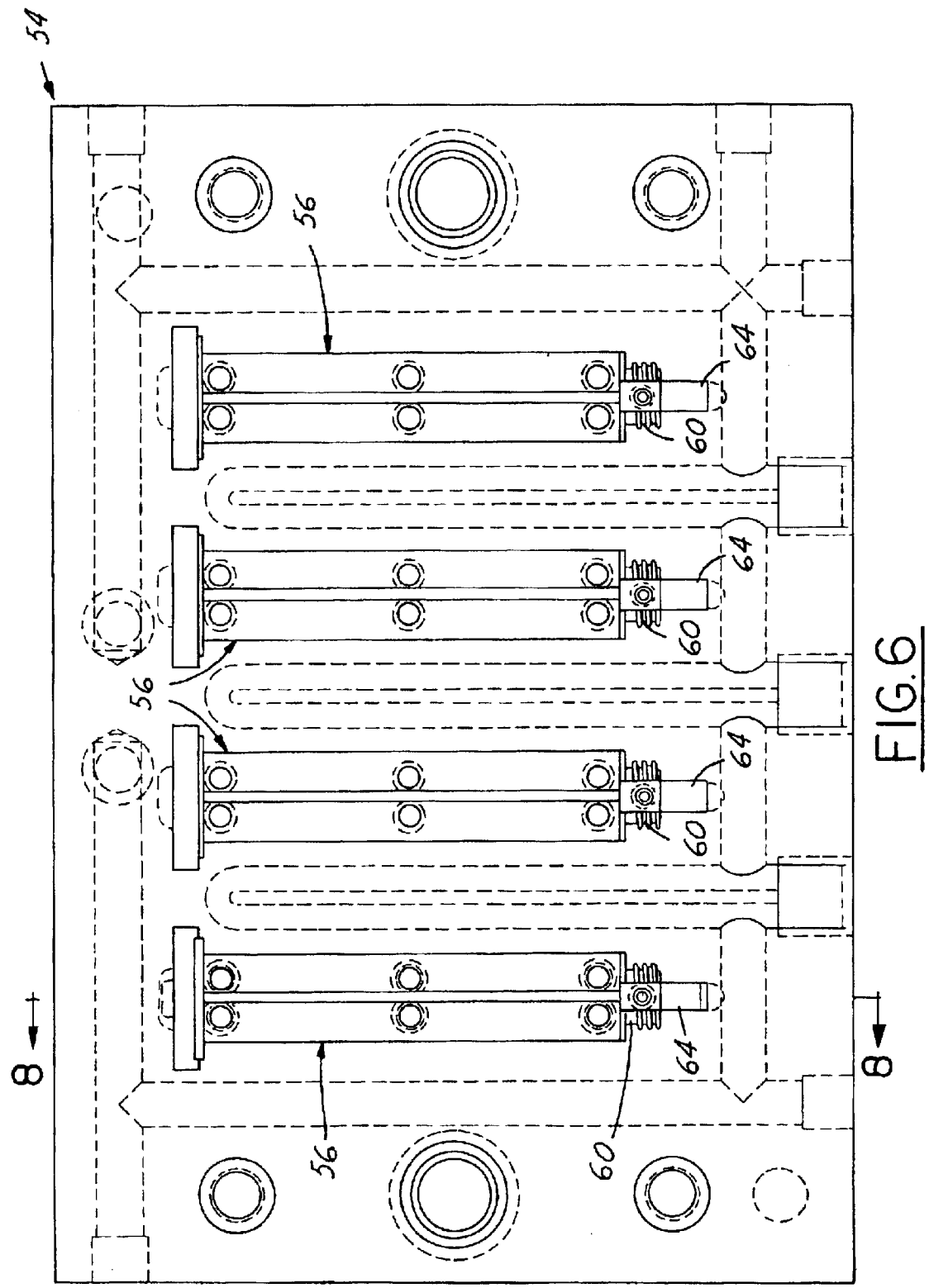

METHOD AND APPARATUS FOR INJECTION MOLDING A THREADED SYRINGE PLUNGER ROD This application is a division of application Ser. No. 09/826,584 filed Apr. 5, 2001 now U.S. Pat. No. 6,494,866.

The present invention is directed to syringes for injection of liquid medicament, and more particularly to manufacture of a plunger rod for such a syringe.

BACKGROUND AND SUMMARY OF THE INVENTION

Syringes of the subject type typically include a barrel for containment of a liquid medicament or solution, a plunger tip slidably disposed within the syringe barrel, and a plunger rod secured to the plunger tip. During automated assembly, a cap is secured to an end of the barrel, the barrel is filled with liquid solution, and the plunger tip is placed in the barrel over the solution. The plunger rod is then secured to the plunger tip. To use the syringe, the cap is removed from the end of the barrel and a needle is threaded onto the barrel. The plunger rod and plunger tip are then manually pushed into the barrel to eject liquid solution from the end of the needle. It is a general object of the present invention to provide a method and apparatus for injection molding the plunger rod that employ a simple mold structure and simple opening/closing actions at the mold structure. Another object of the present invention is to provide a method and apparatus for injection molding a syringe plunger rod that achieve improved plastic material flow and improved filling of the threaded end portion of the plunger rod that is secured to the plunger tip. Another object of the present invention is to provide a plunger rod for a syringe manufactured employing such method and/or apparatus.

A plunger rod for a syringe in accordance with a presently preferred embodiment of the invention is of integrally injection molded plastic construction having an elongated body with a coaxial end portion. An interrupted or segmented external thread extends around the end portion for threaded receipt into a plunger tip that is slidably received in a syringe barrel. A flat extends chordally across the end portion of the rod interrupting the external thread. The plastic, of which the plunger rod is molded, is gated into the mold for the plunger rod at the flat that extends across the rod end portion, leaving a gate mark or vestige on the flat. Gating of the plastic material into the portion of the mold that forms the threaded end portion of the plunger rod achieves improved flow and improved filling of the external thread, while employing a simple and economical mold construction. The gate vestige does not interfere with threading of the plunger rod end portion into the plunger tip. In the preferred embodiment, the end portion of the plunger rod is cored during molding to provide a C-shaped cross section at the rod end portion, which improves dimensional stability during material shrinkage after molding.

A method of making a plunger rod for a syringe, in accordance with a second aspect of the present invention, contemplates providing a mold having at least one mold cavity for molding a plunger rod having a body, an end portion with an external thread and a flat extending chordally across the end portion interrupting the external thread. Plastic material, such as polypropylene, is gated into the mold cavity at this flat such that the plastic material flows to fill the cavity, and the plunger rod is then removed from the mold cavity. A mold for injection molding a plastic syringe plunger rod in accordance with a third aspect of the invention includes a first mold section having a body and a gate insert, and a second mold section having a body and a core insert. The first and second mold sections together form at least one mold cavity. The gate and core inserts form the portion of the mold cavity within which the end portion of the plunger rod is molded. This portion of the mold cavity has a C-shaped axial cross section, with the gate insert forming a flat in a central portion of the C-shaped cross section. Plastic material is gated through the gate insert radially into the end portion of the mold cavity, and then flows axially into the cavity to mold the plunger rod.

BRIEF DESCRIPTION OF THE DRAWINGS

The invention, together with additional objects, features and advantages thereof, will be best understood from the following description, the appended claims and the accompanying drawings in which:

FIGS. 6 and 7 are elevational views of mold half sections for molding the plunger rod illustrated in FIGS. 3–5;

DETAILED DESCRIPTION OF PREFERRED EMBODIMENTS

Figure 1:
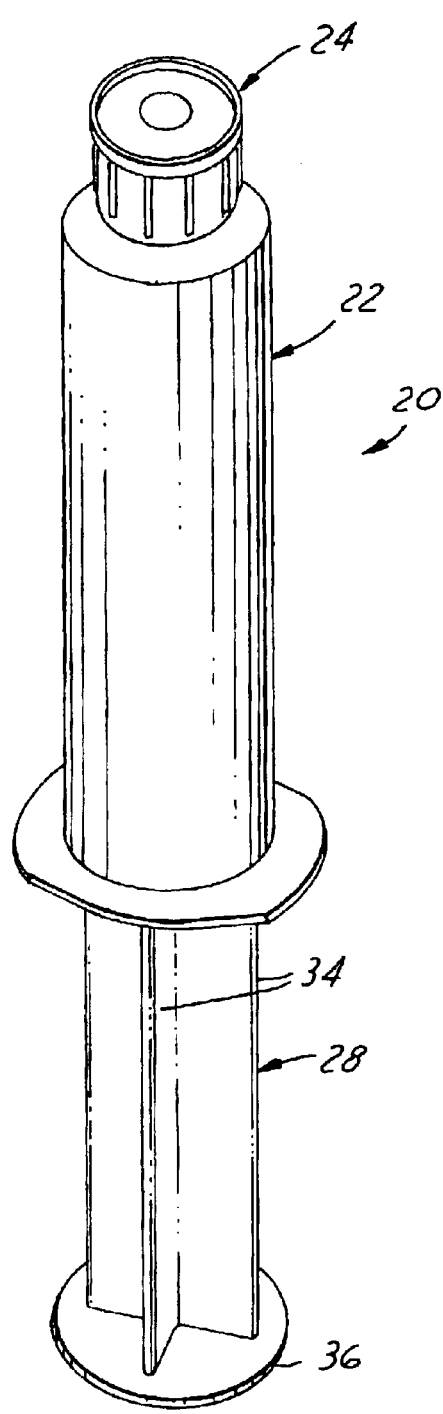
FIG. 1 is a perspective view of a syringe assembly in accordance with a presently preferred embodiment of the invention.
Figure 2:
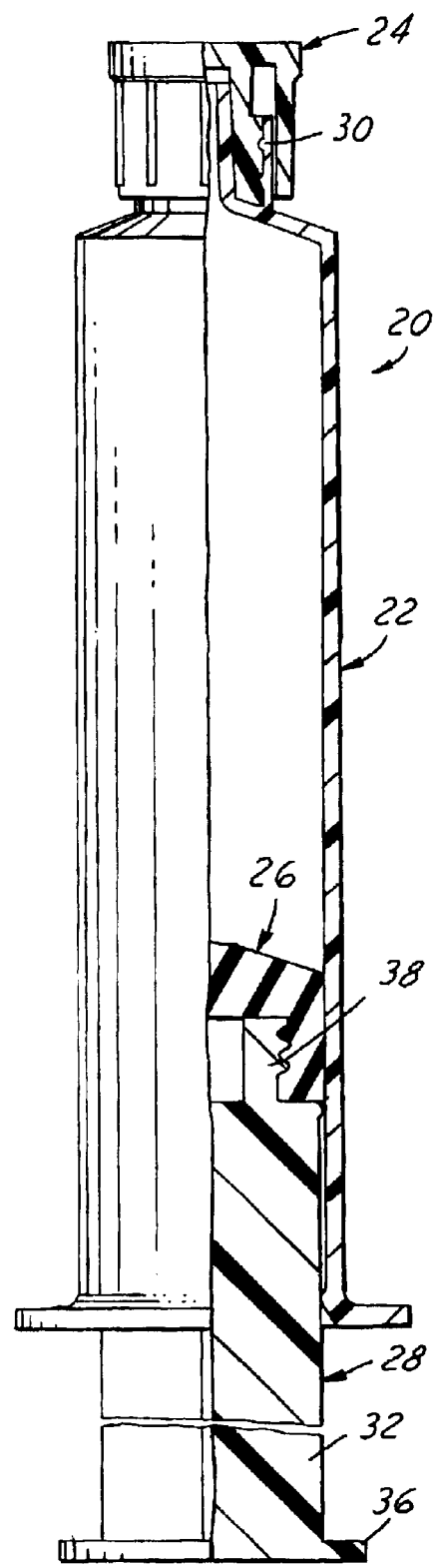
FIG. 2 is a partially sectioned elevational view of the syringe assembly illustrated in FIG. 1.

FIGS. 1–2 illustrate a syringe assembly 20 as including a generally cylindrical barrel 22 having a cap 24 secured over one end. A plunger rod 28 is secured to an internally threaded plunger tip 26 for sliding the plunger tip within the hollow interior of barrel 22. Plunger assembly 20 is typically prefilled with liquid medicament solution. Cap 24 is secured to one end of barrel 22, and the barrel interior is then filled with an appropriate amount of solution. Plunger tip 26 is then inserted into the body of the barrel to seal the solution in place. Plunger rod 28 may be secured to plunger tip 26 at the time of prefilling and assembly, or may be secured to the plunger tip by a user. To dispense the solution within the syringe assembly, cap 24 is removed and a female luer conical connection (not shown) is secured to the end 30 of the barrel. Plunger rod 28 and plunger tip 26 are then manually pushed into barrel 22 to dispense the solution through the luer connection.

Figure 5:
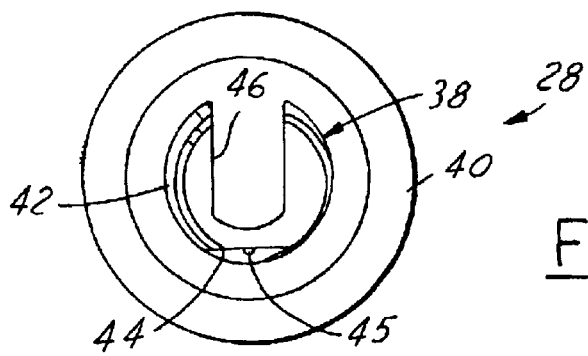
FIGS. 3, 4 and 5 are respective front, side and end views of the syringe plunger rod illustrated in FIGS. 1 and 2.
Figure 3:
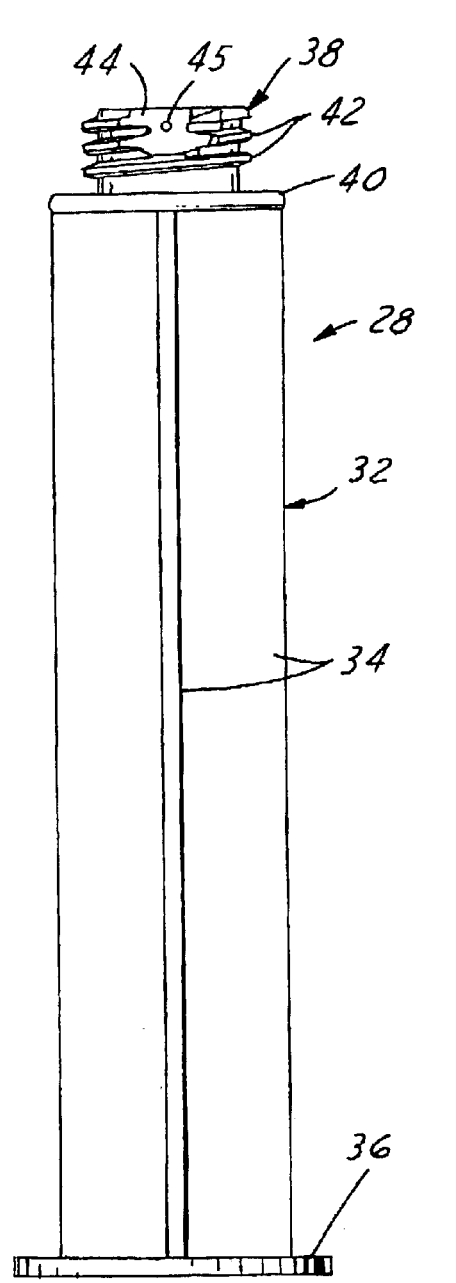
Figure 4:
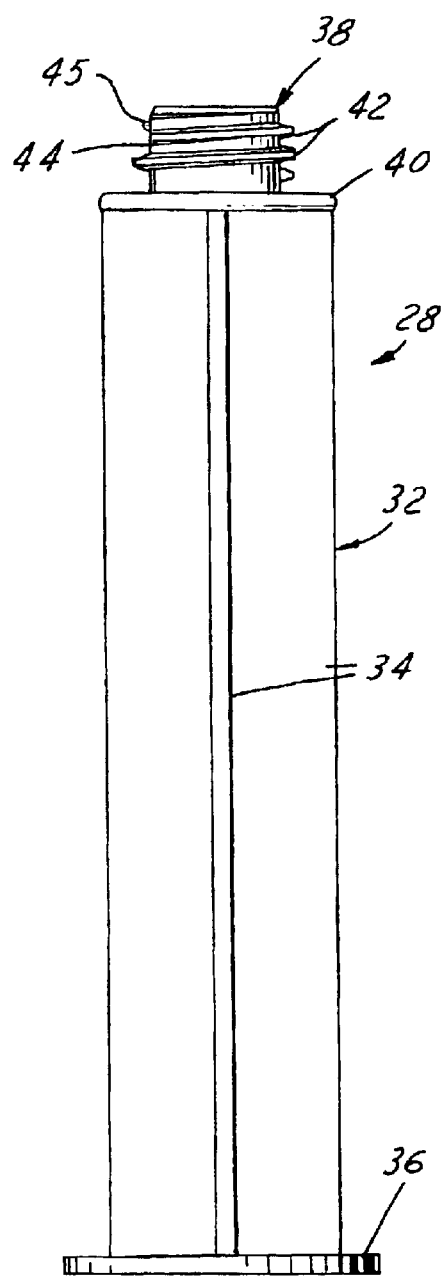
Figure 7:
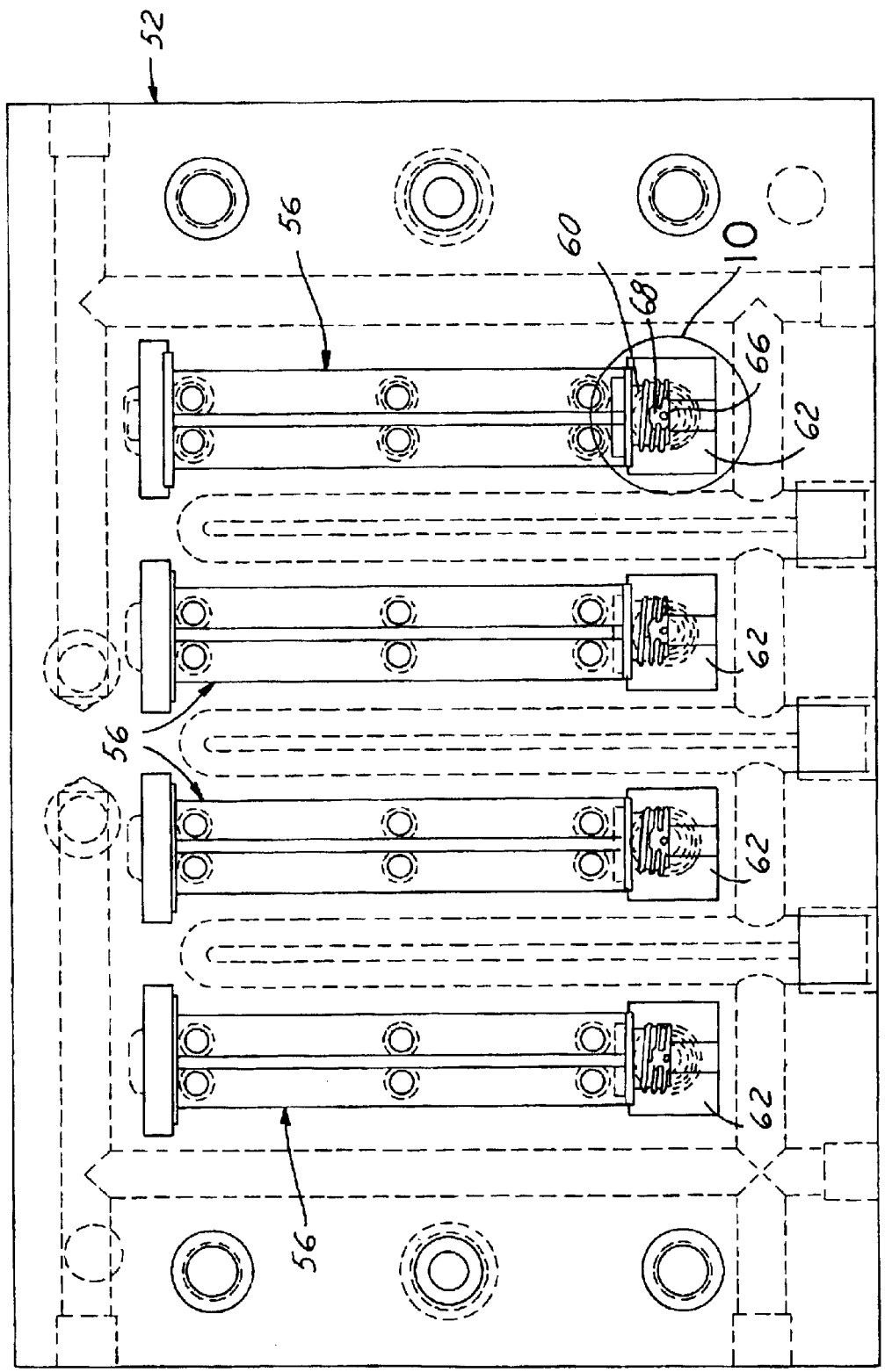

Plunger rod 28 is illustrated in greater detail in FIGS. 3–5. Plunger rod 28 includes an elongated body 32 formed by orthogonally spaced elongated legs 34. A ledge 36 at one end provides a rest for a user's thumb. At the opposing end of body 32, an end portion 38 integrally extends from a ledge 40 coaxially with body 32. End portion 38 has an external thread 42 that extends around the generally cylindrical outer surface contour of end portion 38. A flat 44 extends chordally across the outer surface of end portion 38 interrupting thread 42. Preferably, flat 44 extends axially along only a portion of the outer surface of the syringe end portion, so that at least the turn of thread 42 adjacent to ledge 40 is uninterrupted by flat 44. A gate mark or vestige 45 is disposed on flat 44 where the plastic material is gated into the mold for plunger rod 28, as will be described. Gate vestige 45 may include a small burr, or may simply constitute a mark that is visible on flat 44. However, the dimension of vestige radially of end portion 38 does not interfere with threaded insertion of end portion 38 into plunger tip 26 (FIG. 2). A pocket 46 (FIG. 5) extends diametrically into end portion 38 from a side opposite flat 44 so as to impart a generally C-shaped cross section to end portion 38 as viewed from the axial direction. Flat 44 extends across the exterior of the mid portion of this C-shaped cross section.

Figure 8:
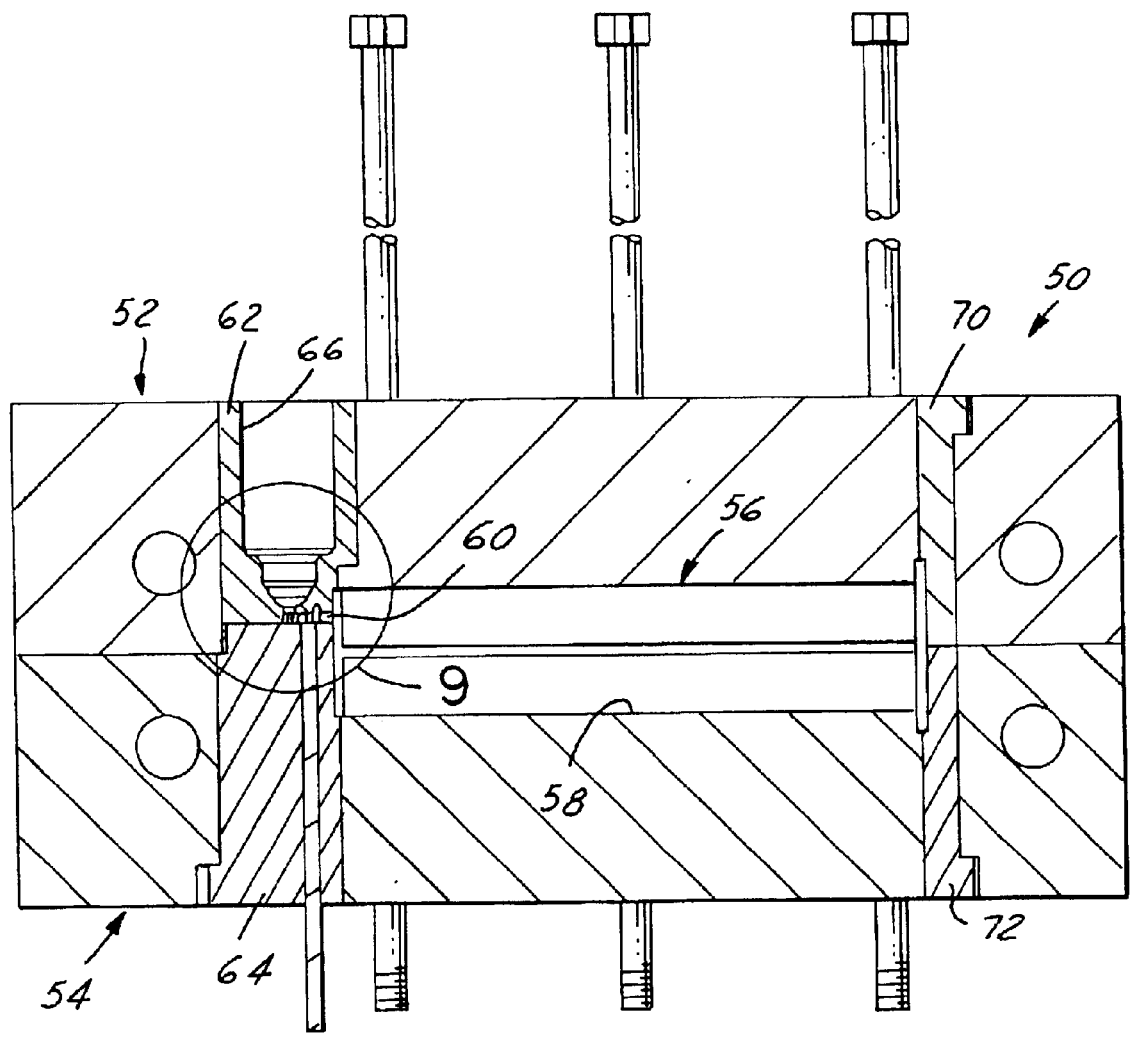
FIG. 8 is a sectional view taken substantially along the line 8—8 in FIG. 6, but showing the mold half sections of FIGS. 6 and 7 in facing engagement.
Figure 9:
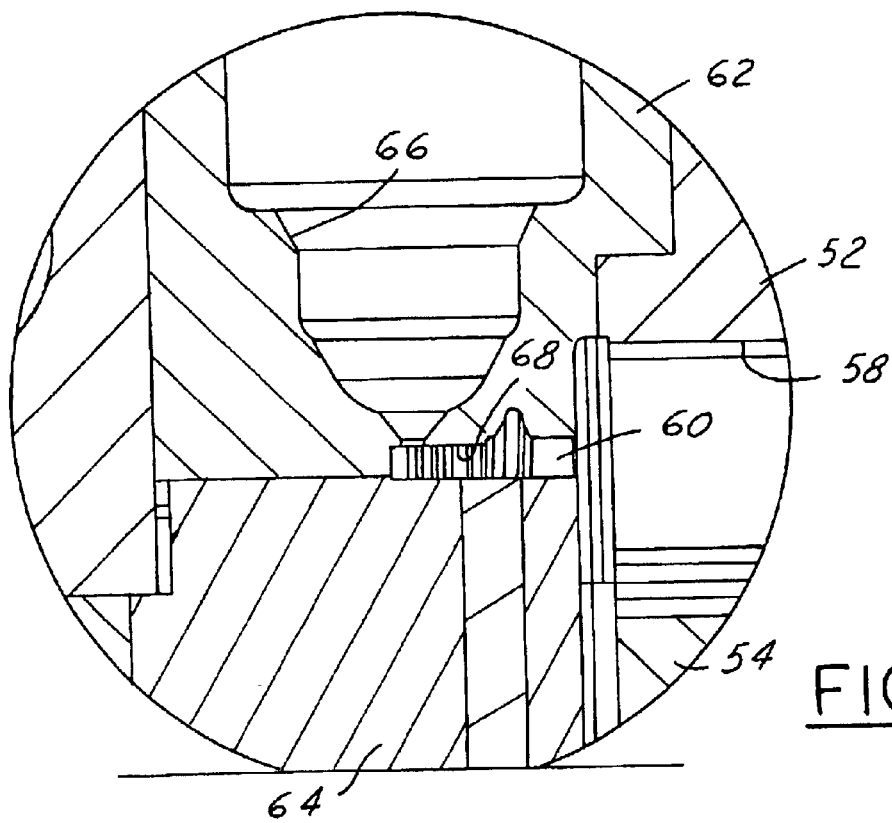
FIG. 9 is an enlarged view of the portion of FIG. 8 within the circle 9.
Figure 10:
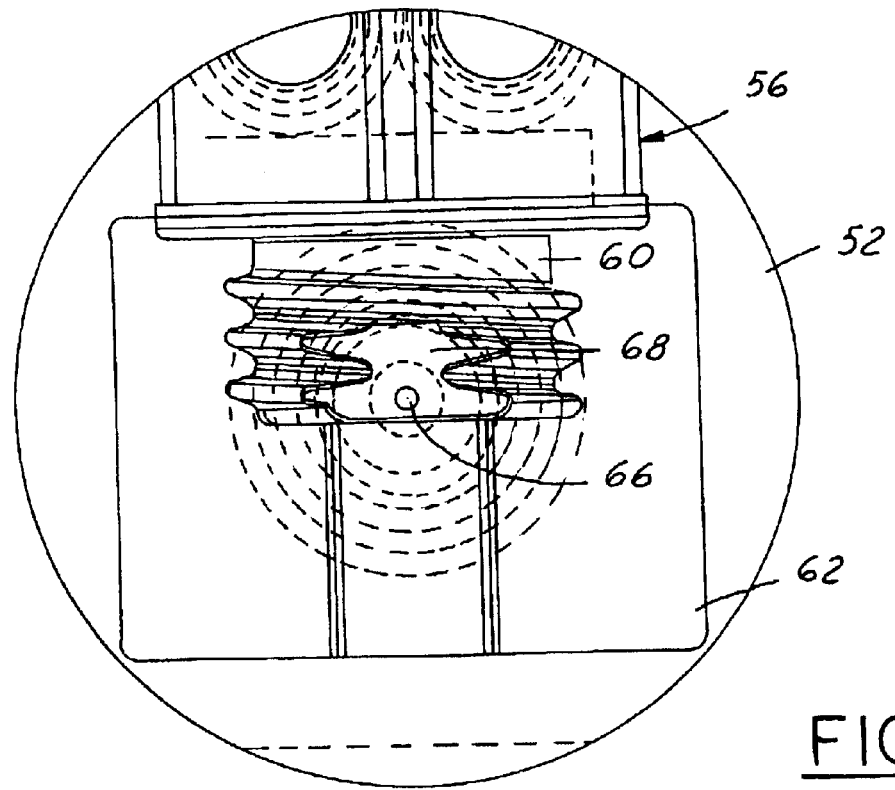
FIG. 10 is an enlarged view of the portion FIG. 7 within the circle 10.

FIGS. 6–10 illustrate a mold 50 for injection molding plunger rod 28. Mold 50 includes a first mold half-section 52 and a second mold half-section 54 brought into facing engagement with each other to form at least one, and preferably a plurality of mold cavities 56 for injection molding the plunger rods. Each mold cavity 56 includes a body portion 58 for forming plunger body 32 with legs 34 and ledges 36,40 (FIGS. 3–5), and an end portion 60 for forming plunger rod end portion 38. End portion 60 of each mold cavity 56 is formed by a gate insert 62 in mold section 52 and an opposed core insert 64 in mold section 54. Gate insert 62 has a radial material flow passage 66 that terminates at a flat insert face 68 (FIGS. 9–10) to form flat 44 on syringe end portion 38. Core insert 64 extends into cavity end portion 60 to form pocket 46 (FIG. 5) in the end portion of the plunger rod. Thus, with mold sections 52, 54 closed, as illustrated in FIG. 8, plastic material such as polypropylene is injected through passage 66 in gate insert 62 into cavity section 60 of cavity 66. This plastic material flows axially through cavity portion 60 into cavity portion 58 for forming the body of the plunger rod. Suitable vent inserts 70, 72 are provided at the opposing ends of mold sections 52, 54 to vent air from the cavity as the plastic material is injected into the cavity. When the cavity is filled with material and allowed partially to cool, the mold sections are opened and the plunger rod(s) are ejected from the mold. Gate vestige 45 (FIGS. 3–5) is left on flat 44 at the point where plastic material enters cavity portion 60 from gate insert passage 66.

There has thus been disclosed an injection molded syringe plunger rod, a method of molding the plunger rod and an apparatus for molding the plunger rod that fully satisfy all of the objects and aims previously set forth. Provision for injection of the plastic material through a flat in the rod end portion provides good flow of material into the mold cavity and excellent filling of the thread portion of the mold cavity. This gating arrangement also accommodates an economical mold structure that may be simply opened and closed to manufacture the parts. Use of core inserts 64 provides good dimensional stability during plastic shrinkage after molding. Although the invention has been disclosed in conjunction with a preferred embodiment thereof, a number of modifications and variations have been suggested. Other modifications and variations will readily suggest themselves to persons of ordinary skill in the art. The invention is intended to embrace all such modifications and variations as fall within the spirit and broad scope of the appended claims.

What is claimed is:

1. A method of making a plunger rod for a syringe, which includes the steps of:
    (a) providing a mold having at least one mold cavity for molding said plunger rod having a body, an end portion with an external thread and a flat extending chordally across said end portion interrupting said external thread,
    (b) gating plastic material radially into said mold cavity at said flat such that the plastic material flows to fill said cavity, and
    (c) removing the plunger rod for the mold cavity leaving a gate vestige at said flat.

2. The method set forth in claim 1 wherein said step (a) includes the steps of:
    (a1) providing a first mold section having a gate insert,
    (a2) providing a second mold section having a core insert, and
    (a3) bringing said first and second mold sections together to form said cavity, with said core insert being opposed to said gate insert to form a portion of said cavity to mold said end portion of said plunger rod, said cavity portion having a C-shaped cross section with said core insert forming an interior of said C-shaped cross section and said gate insert forming said flat in an exterior mid portion of said C-shaped cross section.

3. The method set forth in claim 1 wherein said step (c) is such that said gate vestige on said flat is dimensioned so as to be free of interference with threading of a plunger tip onto said end portion of said plunger rod.

4. The method set forth in claim 1 wherein said step (a) is such that said end portion is C-shaped in cross section axially of said rod, with said flat extending across a mid portion of said C-shaped cross section.

5. The method set forth in claim 4 wherein said step (a) is such that external thread has a plurality of spiral turns on said end portion, and wherein said flat interrupts some but not all of said spiral turns.

6. The method set forth in claim 5 wherein said step (a) is such that said plunger end portion is of lesser diameter than said body, and wherein said external thread has a turn adjacent to said body that is uninterrupted by said flat.

7. A mold for injection molding a plastic syringe plunger rod having a body with an end portion and an external thread, said mold including:
    a first mold section having a body and a gate insert, and
    a second mold section having a body and a core insert,
    said first and second mold sections forming at least one mold cavity in which said gate and core inserts form a portion of said cavity for said end portion of said plunger rod, said portion of said cavity having a C-shaped axial cross section with said gate insert forming a flat in a mid portion of said C-shaped cross section,
    such that plastic gated through said gate insert flows radially and then axially into said cavity through said portion of said cavity.

* * * * *